United States Patent
Bharat et al.

(10) Patent No.: US 9,744,379 B2
(45) Date of Patent: Aug. 29, 2017

(54) STUDYING DOSIMETRIC IMPACT OF MOTION TO GENERATE ADAPTIVE PATIENT-SPECIFIC MARGINS IN EBRT PLANNING

(75) Inventors: Shyam Bharat, Creve Coeur, MO (US); Karl Antonin Bzdusek, Madison, WI (US); Parag Jitendra Parikh, St. Louis, MO (US); Camille Elizabeth Noel, St. Louis, MO (US)

(73) Assignees: KONINKLIJKE PHILIPS N.V., Eindhoven (NL); WASHINGTON UNIVERSITY, St. Louis, MO (US)

(*) Notice: Subject to any disclaimer, the term of this patent is extended or adjusted under 35 U.S.C. 154(b) by 827 days.

(21) Appl. No.: 14/004,504

(22) PCT Filed: Mar. 13, 2012

(86) PCT No.: PCT/IB2012/051178
§ 371 (c)(1),
(2), (4) Date: Sep. 11, 2013

(87) PCT Pub. No.: WO2012/123894
PCT Pub. Date: Sep. 20, 2012

(65) Prior Publication Data
US 2014/0005464 A1 Jan. 2, 2014

Related U.S. Application Data

(60) Provisional application No. 61/452,797, filed on Mar. 15, 2011.

(51) Int. Cl.
*A61N 5/00* (2006.01)
*A61N 5/10* (2006.01)
(52) U.S. Cl.
CPC ......... *A61N 5/1037* (2013.01); *A61N 5/1031* (2013.01); *A61N 2005/1072* (2013.01)

(58) Field of Classification Search
CPC .... A61N 5/103; A61N 5/1039; A61N 5/1045; A61N 2005/1041; A61N 2005/1074
(Continued)

(56) References Cited

U.S. PATENT DOCUMENTS 5,513,238 A * 4/1996 Leber .................. A61N 5/1031
378/65
7,245,698 B2 7/2007 Pang et al.
(Continued)

FOREIGN PATENT DOCUMENTS

| EP | 1905482 A1 | 4/2008 |
| WO | 03092789 A2 | 11/2003 |
| WO | 2010018476 A2 | 2/2010 |

OTHER PUBLICATIONS

Accuray, Inc.; CyberKnife Robotic Radiation Therapy System Advertising Brochure downloaded Aug. 15, 2013 http://www.accuray.com/solutions/treatment-delivery.
(Continued)

*Primary Examiner* — Samuel Gilbert

(57) ABSTRACT

A treatment planning system (106) for generating patient-specific treatment margins. The system (106) includes one or more processors (142). The processors (142) are programmed to receive a radiation treatment plan (RTP) for irradiating a target (122) over the course of one or more treatment fractions. The RTP including one or more treatment margins around the target (122) and a planned dose distribution for the target (122). The processors (142) are further programmed to receive motion data for at least one of the treatment fractions of the RTP from one or more target surrogates (124), calculate a motion-compensated dose distribution for the target (122) using the motion data and the planned dose distribution, compare the motion-compensated dose distribution to the planned dose distribution, and adjust (Continued)

the treatment margins based on dosimetric differences between the motion-compensated dose distribution and the planned dose distribution.

15 Claims, 3 Drawing Sheets

(58) Field of Classification Search
USPC .................................................. 600/1; 378/65
See application file for complete search history.

(56) References Cited

U.S. PATENT DOCUMENTS

| | | | |
|---|---|---|---|
| 8,444,543 B2* | 5/2013 | Fenster | A61B 8/0833 600/3 |
| 8,467,497 B2* | 6/2013 | Lu | A61N 5/1049 378/65 |
| 2007/0041497 A1 | 2/2007 | Schnarr et al. | |
| 2008/0002811 A1* | 1/2008 | Allison | A61N 5/103 378/65 |
| 2009/0116616 A1 | 5/2009 | Lu et al. | |
| 2009/0147916 A1 | 6/2009 | Fallone et al. | |
| 2009/0257577 A1* | 10/2009 | Wu | H04M 1/57 379/207.02 |

OTHER PUBLICATIONS

Aubry, J-F., et al.; Measurements of Intrafaction Motion and Interfraction and Intrafaction Rotation of Prostate by Three-Dimensional Analysis of Daily Portal Imaging with Radiopaque Markers; 2004; Int. J. Radiation Oncology Bio. Phys.; 60(1)30-39.

Hugo, G., et al.; Population and patient-specific target margins for 4D adaptive radiotherapy to account for intra-and inter-fraction variation in lung tumour position; 2007; Phys. Med. Biol.; 52:257-274.

Keall, P.; 4-Dimensional Computed Tomography Imaging and Treatment Planning; 2004; Seminars in Radiation Oncology; 14(1)81-90.

Noel, C. E., et al.; An automated method for adaptive radiation therapy for prostate cancer patients using continuous fiducial-based tracking; 2010; Phys. Med. Biol.; 55(1)65-82.

Willoughby, T. R., et al.; Target Localization and Real-Time Tracking Using the Calypso 4D Localization System in Patients with Localized Prostate Cancer; 2006; Int. J. Radiation Oncology Biol. Phys.; 65(2)528-534.

* cited by examiner

STUDYING DOSIMETRIC IMPACT OF MOTION TO GENERATE ADAPTIVE PATIENT-SPECIFIC MARGINS IN EBRT PLANNING

CROSS REFERENCE TO RELATED APPLICATIONS

This application is a national filing of PCT application Serial No. PCT/IB2012/051178, filed Mar. 13, 2012, published as WO 2012/123894 A1 on Sep. 20, 2012, which claims the benefit of U.S. provisional application Ser. No. 61/452,797 filed Mar. 15, 2011, which is incorporated herein by reference.

This invention was made with government support under grant CA134541 awarded by the National Institutes of Health. The government has certain rights in the invention.

The present application relates generally to external beam radiation therapy (EBRT). It finds particular application in conjunction with generating patient-specific treatment margins, and will be described with particular reference thereto. However, it is to be understood that it also finds application in other usage scenarios, and is not necessarily limited to the aforementioned application.

In external beam radiation therapy (EBRT), spatially targeted doses of radiation are applied to tumors or other targets containing cancerous or malignant tissue. Growing and rapidly multiplying cancer cells tend to be more susceptible to damage from radiation, as compared with normal cells, such that dosages administrated by proper planning preferentially kill cancerous or malignant tissue. To ensure tumors or other targets are fully irradiated, radiation treatment plans (RTPs) are typically planned with treatment margins around the tumors or other targets. Standard protocol utilizes generic population-based treatment margins for all patients. While these treatment margins are designed to ensure complete coverage of a tumor or other target, they can result in overdosing of organs at risk (OARs) or other regions. Therefore, EBRT typically balances the need for complete destruction of tumors or other targets against the need to reduce margins to spare surrounding organs at risk (OARs) or other regions from radiation damage.

One benefit of reducing treatment margins is that treating with smaller margins allows dose escalation in a tumor or target. However, a major inhibiting factor to treatment margin reduction is the presence of tissue motion, both during and in-between treatment sessions (or fractions). Therefore, the management of motion, especially in relation to tumors or other targets, is of utmost importance in ensuring the successful delivery of radiation.

Before administering a treatment fraction, the patient is generally aligned on a treatment couch using lasers on skin marks and/or radiographic imaging. In some cases, cone beam computerized tomography (CBCT) imaging is additionally used prior to treatment. All these techniques are aimed to correct for interfraction motion. Solely adjusting for interfraction motion, however, does not provide a complete measure of confidence in dose delivery. To address this, there exist methods to track the position of a tumor or other target during treatment (intrafraction motion). These methods include fluoroscopic imaging of implanted fiducial markers and electromagnetic (EM) tracking of implanted transponders at a high temporal rate (e.g., 10 Hz). The implanted fiducials and/or the implanted transponders serve as a surrogate for the tumor or other target. Methods such as these not only provide positional information of the tumor or other target during treatment, but also initial deviations of the tumor or other target at the beginning of each fraction relative to a radiation treatment plan (RTP) and/or previous fractions. During treatment, the positional information of the transponders or fiducials can be utilized in different ways to adjust the treatment paradigm, one of which is to manually turn off the radiation beam if the target is deemed to exceed pre-defined boundaries.

Though the above-mentioned measures reduce the variability in the delivery of a planned dose distribution, interfraction and/or intrafraction motion information obtained from these methods is generally not utilized to study the impact of the motion after treatment. In that regard, the resulting impact of motion on the delivered dose is an important yardstick by which the success of the treatment can be classified. Small motion patterns (which may not be construed to be significant during treatment) can cumulatively result in a delivered dose that is significantly different from the planned dose distribution.

The present application provides new and improved methods and systems which overcome the above-referenced problems and others.

In accordance with one aspect, a treatment planning system for generating patient-specific treatment margins is provided. The system includes one or more processors programmed to receive a radiation treatment plan (RTP) for irradiating a target over the course of one or more treatment fractions. The RTP includes one or more treatment margins around the target and a planned dose distribution for the target. The processors are further programmed to receive motion data for at least one of the treatment fractions of the RTP from one or more target surrogates. The motion data for at least one of the treatment fractions need not include motion data for an entire treatment fraction. The processors are further programmed to calculate a motion-compensated dose distribution for the target using the motion data and the planned dose distribution, compare the motion-compensated dose distribution to the planned dose distribution, and adjust the treatment margins based on dosimetric differences between the motion-compensated dose distribution and the planned dose distribution.

In accordance with another aspect, a method for generating patient-specific treatment margins is provided. A radiation treatment plan (RTP) for irradiating a target is received over the course of one or more treatment fractions. The RTP includes one or more treatment margins around the target and a planned dose distribution for the target. Motion data for at least one of the treatment fractions of the RTP is received from one or more target surrogates. The motion data for at least one of the treatment fractions need not include motion data for an entire treatment fraction. A motion-compensated dose distribution for the target is calculated using the motion data and the planned dose distribution. The motion-compensated dose distribution is compared to the planned dose distribution. The treatment margins are adjusted based on dosimetric differences between the motion-compensated dose distribution and the planned dose distribution.

One advantage resides in calculating a radiation dose actually delivered to a patient.

Another advantage resides in more accurate delivery of radiation to a target region.

Another advantage resides in more accurately determining a radiation dose actually delivered to target and non-target tissue.

Another advantage resides in improvement in radiotherapy treatment planning workflows used in medical institutions.

Another advantage resides in a reduction in mid-treatment imaging.

Another advantage resides in the calculation of patient-specific treatment margins and target dose escalation.

Another advantage resides in reducing the risk of normal tissue damage.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
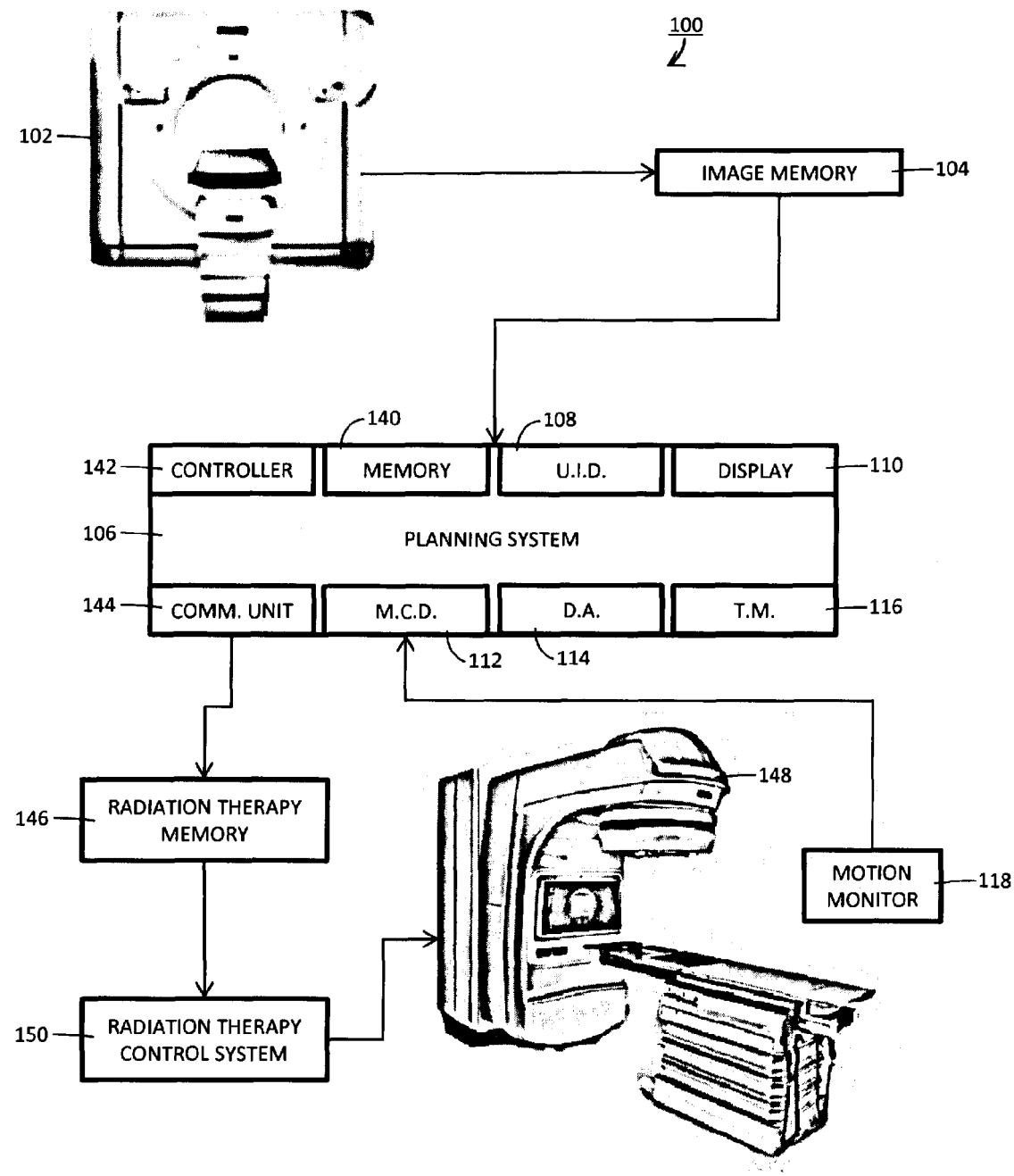
FIG. 1 is a radiation therapy system in accordance with aspects of the present disclosure.

With reference to FIG. 1, a radiation therapy system 100 for treating patients is provided. The radiation therapy system is employed to provide radiation therapy to a patient, such as one or more of external beam radiation therapy, proton therapy, ablation therapy and high-intensity focused ultrasound therapy. The radiation therapy system 100 includes one or more imaging modalities 102 suitable for acquiring images embodying objects of interest (OOIs), such as regions of interest (ROIs) and points of interest (POIs), within the patients. The imaging modalities 102 suitably include a computed tomography (CT) scanner. However, the imaging modalities 102 can additionally or alternatively include one or more of a positron emission tomography (PET) scanner, a magnetic resonance (MR) scanner, a single photon emission computed tomography (SPECT) scanner, and the like.

Images acquired from the imaging modalities 102 are typically three-dimensional images. However, two-dimensional images are contemplated. Three-dimensional images typically include a stack of two-dimensional images, hereafter referred to as slices. Further, images acquired from the imaging modalities 102 are stored in an image memory 104. Typically, the image memory 104 is a central records storage system. However, it is contemplated that the image memory 104 is local to the imaging modalities 102 or another component of the radiation therapy system 100. Insofar as the image memory 104 is remote from the imaging modalities 102, the imaging modalities 102 are suitably connected therewith via a communications network, such as a local area network (LAN).

A planning system 106 of the radiation therapy system 100 receives planning images for each of the patients and employs the images to generate and/or update radiation therapy treatment plans (RTPs) and/or to perform post-treatment analysis of RTPs. A planning image is an image used to generate and/or update an RTP. Typically, the images are acquired from the image memory 104 and/or the imaging modalities 102. However, the images can be acquired from other sources. Further, the planning images are typically received electronically via a communications network. However, other means of receiving the planning images are contemplated. Suitably, the planning system 106 provides typical treatment planning functionalities, such as manual and automated segmentation tools, image fusion tools, three-dimensional conformal radiotherapy (CRT) planning tools, inverse intensity-modulated radiation therapy (IMRT) optimization tools, dose calculation tools, and so on.

To generate an RTP for a patient, the planning system 106 receives one or more planning images before radiation therapy. The planning images are suitably focused on one or more tumors or other targets of the patient to be treated or observed. Further, the planning images are suitably three-dimensional and include a plurality of slices (or two-dimensional images).

Upon receiving the planning images, a contour (or trajectory) is identified around each of the tumors or other targets and one or more OARs or other regions. Contouring is used to delineate between the tumors or other targets and the OARs or other regions and between the OARs and the other regions. An oncologist or other clinician suitably performs the contouring. However, automated and semi-automated approaches are contemplated. Insofar as a clinician performs or asserts the contouring, the clinician suitably employs one or more user input devices 108 to identify the contours on a graphical user interface presented via a display 110. For example, the graphical user interface can display a planning image and allow the clinician to draw or mark the contours on the planning image using the user input devices 108. Typically, one or more treatment margins are automatically added around the contoured regions to account for interfraction and/or intrafraction motion. As noted above, these treatment margins have traditionally been generic population-based treatment margins.

In addition to identifying the contours, radiation plan parameters are defined for the contoured regions. Suitably, the clinician or oncologist defines the radiation plan parameters via the graphical user interface. For example, the clinician defines the radiation plan parameters using the user input devices 108. However, as with contouring, automated approaches are contemplated. The radiation plan parameters typically include minimum or target doses to be delivered to the tumors or other targets, maximum permissible doses for the OARs or other regions, and the like.

The radiation therapy plan parameters, together with known information about radiation attenuation or absorption characteristics of the various tissues and the contoured tumors or other targets and the contoured OARs or other regions, are used to generate the RTP. As discussed below, the RTP defines trajectories along which the radiation beam irradiates the targets, the radiation beam spatial projection of each radiation beam trajectory, the intensity of the radiation beam along each trajectory, the duration the targets are irradiated along each trajectory, or the like. In certain embodiments, the RTP is optimized for the particular type of radiation therapy, such as external beam radiation therapy, proton therapy, ablation therapy and high-intensity focused ultrasound therapy.

During each radiation therapy session, the cumulative dose of radiation delivered to tumors or other targets and OARs or other regions is determined. As the therapy session progress, the tumors or other targets typically shrink and the OARs or other regions typically shift, potentially causing errors in the accumulated dose calculations and the contours (or trajectories). The RTP and the integration of cumulative radiation dose delivered to the tumors or other targets and the OARs or other regions assumes the locations and sizes of the tumors or other targets and the OARs or other regions remain as is in the images on which the RTP is based. If these locations or sizes change, the cumulative radiation doses will have inaccuracies. Therefore, to maintain accuracy, the RTP is periodically updated. Although RTPs are typically updated between treatment fractions, it is contemplated that RTPs are updated during treatment fractions.

To update an RTP for a patient, the planning system 106 typically receives one or more new planning images. For example, the planning system 106 receives planning images after each, or a predetermined number of, radiation therapy sessions (or fractions). As above, the planning images are suitably focused on one or more tumors or other targets of the patient. Upon receiving a new planning image, or upon receiving a predetermined number of new planning images, the contours (or trajectories) and/or the doses of the RTP are typically updated through comparison of the new planning images to the planning images used to generate the RTP and/or previous fractions. Additionally or alternatively, in certain embodiments, the treatment margins of the RTP are tailored to the patient using a motion compensated dose module 112, a dosimetric analysis module 114, and a treatment margins module 116 of the planning system 106. As used herein, tailoring a dose distribution to a patient is to be construed as a form of tailoring treatment margins to a patient.

The motion compensated dose module 112 calculates doses actually delivered to a patient (hereafter referred to as motion-compensated dose distributions) during one or more fractions of an RTP based on motion data of a patient collected during and/or between the fractions. The treatment margins module receives the RTP from, for example, the planning system 106. A motion monitor 118 generates motion data indicative of motion of the tumors or other targets and/or the OARs or other regions, relative to previous fractions and/or the RTP. In that regard, the motion data is typically defined in the coordinate frame of the planning images employed to generate the previous fraction and/or the RTP.

The motion data is typically received from one or more surrogates for the tumors or other targets (hereafter referred to as target surrogates). For example, the motion data is received from three target surrogates disposed at different locations within the patient. In certain embodiments, the target surrogates are RF transponders disposed closely adjacent to the target. The motion monitor 118 in one embodiment includes radio receivers at each of a plurality of surrounding locations which monitor the signals from the transponders for phase shifts or other indicators of displacement and triangulate the location of each transponder. From the spatial relationship between the transponders and the target, indicated in the most recent planning images, displacement or a change in shape of the targets is determined. In other embodiments, the target surrogates are fiducial markers implanted in the patient. In one embodiment, the motion monitor 118 includes an imaging device, such as projection x-ray imaging, magnetic resonance imaging (MRI), CT imaging, or the like, operating, for example, in a fluoroscopic mode. Displacement of the fiducials is determined by analyzing the fluoroscopic images. In certain embodiments, target surrogates are not employed. Rather, image-based motion tracking is employed to receive the motion data. In one embodiment, the motion monitor 118 includes an imaging device, as above, that facilitates image-based motion tracking of the target in real-time using, for example, contours or anatomical structures.

The motion data can be received continuously, on-demand, upon the occurrence of an event, such as a timer event, and so on, but is typically received periodically during radiation therapy, such as at a frequency of 10 Hz. Where the motion data is received continuously, it is suitably broken into discrete blocks based on time and a trending algorithm, such as minimum, median, maximum, mean, and so on, is applied to the discrete blocks.

Figure 2:
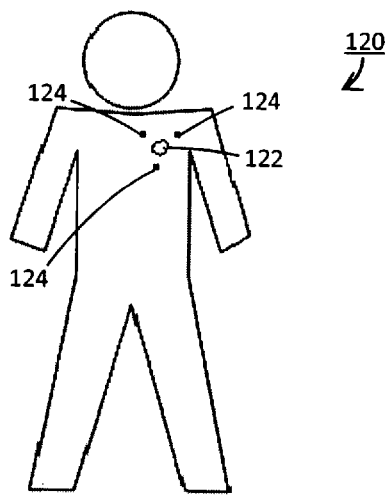
FIG. 2 illustrates an example of a patient undergoing radiation therapy on a tumor or other target.

With reference to FIG. 2, an example of a patient 120 undergoing radiation therapy with the radiation therapy system 100 is provided. The patient 120 has a tumor or other target 122, proximate to which three target surrogates 124, such as transponders and fiducial markers, are implanted or affixed. The target surrogates 124 provide the motion compensated dose module 112 with the motion data while the patient 120 undergoes one or more treatment fractions.

Referring back to FIG. 1, contemporaneous with or after motion data is collected, the motion compensated dose module 112 calculates motion compensated dose distributions. In certain embodiments, this includes, for each time step (or sample) of collected motion data, estimating rigid motion of the target surrogates relative to the most recent planning image used to generate the RTP for the fraction associated with the time step. For example, suppose motion data for three target surrogates is collected over the course of two treatment fractions. A motion estimate is determined for the target and cuticle tissues relative to the most recent planning image used for the first fraction. The motion estimate shows the range of locations over which the target moved and frequency with which the target was in each location. Rigid motion components include translations and rotations. Non-rigid motion can also be employed.

After determining the motion estimates, a cumulative motion pattern for the tumor or other target during at least a portion of a fraction is determined. Typically, however, the cumulative motion pattern is determined for a fraction. For example, one or more probability density functions (PDFs) are created for each of the tumors or other targets based on the motion estimates. The PDF or other deterioration model is created by applying each of the motion estimates associated with the tumor or other target and the treatment fraction to the tumor or other target to yield a motion-compensated location, e.g., a probability that the target is in a given location. The motion of the tumor or other target are accumulated into a PDF to determine the cumulative motion pattern of the tumor or other target during the fraction. The more motion data samples collected during a treatment fraction, the more accurate a PDF. Application of a motion estimate to a tumor or other target shows a portion of the time during irradiation with the treatment beam that the target was all or partially out of the treatment beam and which portions were out for how long.

For each of the PDFs, the planned dose distribution corresponding to the PDF is convolved with the PDF to determine a motion compensated dose distribution for the fraction(s) corresponding to the PDF. The planned dose distribution corresponding to a PDF is the dose distribution intended for the tumor or other target of the PDF during the treatment fraction(s) of the PDF. The motion-compensated doses for a tumor or other target can be accumulated until the end of a portion (or subset) of a fraction, one fraction, or a subset of the fractions.

The original plan dose calculation typically assumes that the target is stationary during a treatment fraction. Due to the motion the target may not actually receive the calculated dose. For example, if the motion caused the target to be completely out of the treatment beam 10% of the time, then the calculated accumulated dose would be higher than the dose that was actually received by about 10%. The PDF or other motion model will more likely show which portions of the target were out of the beam for what percent of time. By applying the PDF, the actually delivered dose is determined on a statistical basis. The subsequent fractions can then be planned based on the actual dose that was previously delivered.

The subsequent fractions can be adjusted in various ways. For example, the cross section of the therapy beam can be increased in appropriate directions such that the target remains in the treatment for at least a preselected fraction of the time. On the other hand, if the target does not leave the therapy beam, the PDF or other motion model will show if and in which directions the cross section of the beam can be reduced. In a nominal patient, the cross section of the therapy beam is 20-30% larger than the theoretical cross section for a stationary target. If the present patient moves less than average the cross section can be reduced, e.g., to have only a 10-15%) over scan. If the patient moves more than average, the cross section can be increased correspondingly.

During each fraction, the therapy beam irradiates the patient along a plurality of trajectories. The PDF is determined for each trajectory and the beam cross section adjustments can be made independently for each trajectory. Another RTP adjustment for fractions can include a change in the trajectories or a change in the amount of irradiation along each trajectory.

The dosimetric analysis module 114 compares the motion compensated dose distributions of the tumors or other targets to corresponding planned dose distributions qualitatively or quantitatively. Typically, but not necessarily, the motion compensated dose distributions are received from the motion compensated dose module 112. In certain embodiments, if significant dosimetric deviations from the planned dose distributions are detected, imaging is performed using the imaging modalities 102 as a reality check on the motion compensated dose distributions.

To qualitatively compare a motion compensated dose distribution of a tumor or other target with the planned dose distribution, the motion compensated dose distribution and the planned dose distribution are graphically displayed on a graphical user interface presented to an oncologist or other clinician via the display 110. In certain embodiments, the dose distributions are displayed adjacent to one another, such as side-by-side. In other embodiments, the dose distributions are displayed overlaid on one another with varying transparencies. Suitably, color is employed to identify dose intensity. For example, a gradient is employed to identify relative intensity, where the darker the color the greater the intensity. Further, the contours (or trajectories) can be overlaid thereon. Using the user input devices 108, the clinician can sequentially advance through the slices in any dimension (e.g., transverse, sagittal, coronal, oblique, etc.) and observe the resulting two-dimensional dose distributions for a slice. Slices or projections transverse to one or more therapy beam trajectories are contemplated. Advantageously, this can help identify obvious and/or large-scale differences in dose and their spatial locations. In other words, this can help identify hot spots and/or cold spots. A hot spot is an area where more radiation than expected was received, and a cold spot is an area where less radiation than expected was received. In certain embodiments, the qualitative comparison further includes receiving comparison data from the user input devices 108, the comparison data indicating dosimetric differences between the dose distributions, such as the degree of similarity of the dose distributions, the location of hot spots and/or cold spots, and so on.

Figure 3:
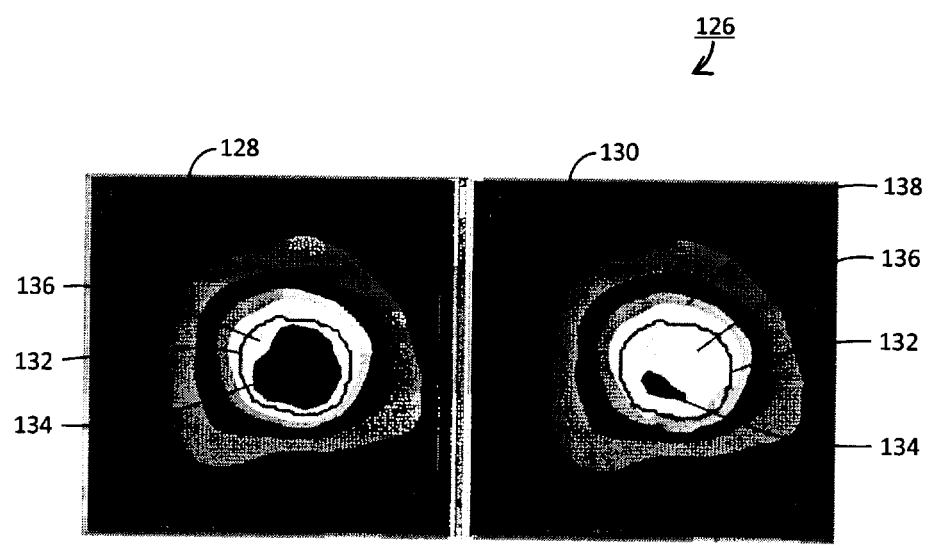
FIG. 3 illustrates one embodiment of a graphical user interface according to aspects of the present disclosure.

With reference to FIG. 3, one embodiment of the graphical user interface 126 is provided. Therein, the planned dose distribution 128 is displayed side-by-side with the actual motion compensated dose distribution 130. The dose distributions 128, 130 are spatially represented with the contour 132 of the target overlaid thereon. As illustrated, the RTP planned to deliver a highest dose 134 over substantially all of target contour 132. However, the actually delivered dose distribution 130 shows that the highest dose 134 was only delivered to a small portion of the target contour 132. A next lower dose 136 was delivered to most of the target region. Moreover, a still lower dose 138 was delivered to the target contour 132 near its lower right edge and the lower edge.

To quantitatively compare the dose distributions, a number of different approaches are contemplated. In certain embodiments, a difference between a planned dose distribution and a motion compensated dose distribution is calculated. The difference provides information regarding the presence of cold spots (or hot spots) in terms of at least one of magnitude, location and extent. Thresholds can, for example, be applied to the difference to identify cold spots and/or hot spots. Additionally or alternatively, in certain embodiments, one or more of dose volume histograms (DVHs), maximum doses, mean doses, minimum doses, etc. of both dose distributions are compared. Additionally or alternatively, in certain embodiments, the dosimetric impact of motion is quantified as a weighted combination of the above factors, with the weights decided by an oncologist or other clinician.

The treatment margins module 116 generates patient-specific treatment margins through adaptation of original treatment margins of an RTP. The treatment margins module 116 receives the RTP from, for example, the planning system 106. That is, based on the PDF or other measurement of the motion of the target(s), the margin or cross section of the therapy beam beyond the theoretical dose section for a stationary target is increased or decreased. When the PDF shows large amounts of motion or motion patterns in which the target spends large portions of the time near the extremes of motion, the margin and the cross section are increased relative to a nominal portion. Conversely, if the target moves very little, the margin and cross section can be decreased. Moreover, the margin can be increased in some directions and decreased in other others. A similar margin adjustment calculation is made for each trajectory along which the therapy beam irradiates the target during a fraction.

Further, the treatment margins module 116 receives one or more motion compensated doses, typically from the motion compensated dose module 112. Thereafter, the treatment margins module 116 suitably employs the dosimetric analysis module 114 to compare the motion compensated dose distributions to the planned dose distributions. However, it is contemplated that the treatment margins module 116 compares the motion compensated dose distributions to the planned dose distributions without the dosimetric analysis module 114.

Based upon the comparison, the treatment margins of the RTP are modified accordingly. In case of one or more cold spots that are deemed to be unacceptable, the margins nearest the cold spots can be increased on the same slice and/or on neighboring slices. In case of one or more hot spots that are deemed to be unacceptable, the margins nearest the hot spots can be decreased on the same slice and/or on neighboring slices. In case of negligible dose differences, margins overall can be reduced by a clinically-determined factor. In certain embodiments, the clinically determined factor is a percentage. It is contemplated that an oncologist defines what is unacceptable and/or negligible using the user input devices 108 and, optionally, the display 110. In certain embodiments, modification of existing margins is performed automatically using, for example, a rules engine. However, manual adjustment of existing margins by an oncologist or other clinician is contemplated.

Where margins are adjusted manually, the treatment margins module receives adjustment data from the user input devices 108. Adjustment data is data indicative of which treatment margins to adjust and how to adjust them. For example, adjustment data can specify to increase a treatment margin proximate a cold spot. In certain embodiments, a graphical user displayed on the display 110 is employed to facilitate the manual modification of the treatment margins. For example, a graphical user interface similar to the graphical user interface employed by the dosimetric analysis module can be employed.

When patient-specific treatment margins are generated using the treatment margins module 116, the patient-specific treatment margins can be employed for remaining treatment sessions of an RTP. If the new dose distribution exhibits reduced coverage of tumors or other targets or increased dosage for OARs or other regions, the margins can be re-evaluated. In that regard, patient-specific treatment margins can be generated iteratively using the treatment margins module 116 until a margin resulting in a satisfactory dose distribution is achieved. Further, dosimetric checks can be performed using, for example, one of the imaging modalities 102 to verify the patient-specific treatment margins.

To perform a post-treatment analysis of an RTP, the planning system 106 receives one or more images after the RTP has completed and/or motion data, as described above. The images are suitably focused on one or more tumors or other targets of the patient. Upon receiving the new images and/or the motion data, at least one of the motion compensated dose module 112, the dosimetric analysis module 114, and the treatment margins module 116 is employed to analyze the RTP. The motion corrected cumulative dose values are determined. The RTP is adjusted in accordance with the new image, the cumulative dose, the motion model, and the like. For example, the treatment margins module 116 can be employed to generate patient-specific treatment margins. As another example, the dosimetric analysis module 114 can be used to study the effect of motion on the RTP.

The planning system 106 suitably includes one or more memories 140 and one or more processor-based controllers 142. The memories 140 store executable instructions for controlling a processor of the processor-based controllers 142 to perform one or more of the abovenoted functions of the planning system 106. Further, in certain embodiments, at least one of the motion compensated dose module 112, the dosimetric analysis module 114, and the treatment margins module 116 is embodied by executable instructions stored in, for example, the memories 140. The processor-based controllers 142 execute the executable instructions stored on the memories 140 to carry out the functions associated with the planning system 106. Where the planning system 106 is operative to perform at least one of receive images from a communications network, store RTPs over a communications network, and receive motion data from a communications network, the planning system 106 further includes one or more communications units 144 facilitating communication between the processor-based controllers 142 and the communications networks.

The RTPs generated and/or updated by the planning system 106 are stored in a radiation therapy plan memory 146. Typically, the radiation therapy plan memory 146 is the central records storage system. However, it is contemplated that the radiation therapy plan memory 146 is local to the planning system 106 or another component of the radiation therapy system 100. Insofar as the radiation therapy plan memory 146 is remote from the planning system 106, the radiation therapy plan memory 146 is suitably connected therewith via a communications network, such as a local area network (LAN).

At a scheduled day and time for a radiation therapy session or fraction of an RTP, a radiation therapy apparatus 148 is employed to deliver therapeutic radiation to the patient. The radiation can include x-rays, protons, sound, and so on suitable for radiation therapy, such as external beam radiation therapy, proton therapy, ablation therapy and high-intensity focused ultrasound therapy. Suitably, the radiation therapy apparatus 148 is controlled by a radiation therapy control system 150 in accordance with the RTP stored in the radiation therapy plan memory 146. For example, in the illustrated embodiment, the radiation therapy delivery apparatus 148 includes a linear accelerator (LINAC), and the radiation therapy control system 150 operates multi-leaf collimator (MLC) or other radiation beam pro file-shaping apparatus of the LINAC to modulate beam intensity and profile as the linear accelerator is moved or stepped around the subject, so as to deliver a radiation dose distribution into the subject that provides the desired integrated radiation dosage to the target feature while suitably limiting or constraining radiation exposure of sensitive critical features in accordance with the RTP.

While the motion-compensated dose module 112, the dosimetric analysis module 114, and the treatment margins module 116 were described together, it is to be appreciated that the modules 112, 114, 116 can be employed separately. Further, it is to be appreciated, that the modules 112, 114, 116 have broader applicability than radiation therapy systems. That is to say, the modules 112, 114, 116 can be employed for purposes other than radiation therapy.

Figure 4:
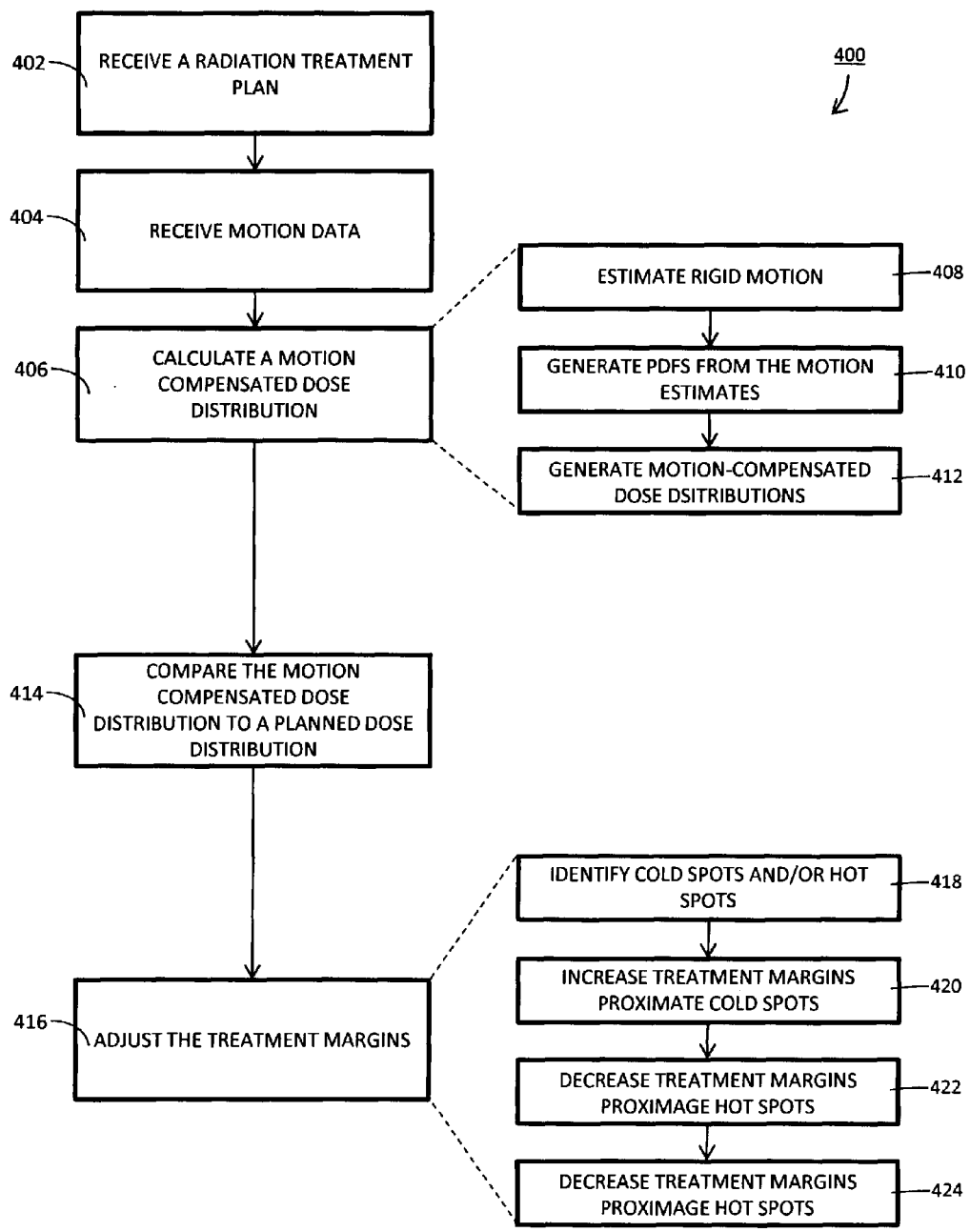
FIG. 4 depicts a method for generating patient-specific treatment margins according to aspects of the present disclosure.

With reference to FIG. 4, a block diagram of a method 400 performed by one or more processors to generate patient-specific treatment margins is provided. A radiation treatment plan (RTP) for irradiating a target over the course of one or more treatment fractions is generated or received 402. The RTP includes one or more treatment margins around the target and a planned dose distribution for the target. During at least one of the treatment fractions, motion data is received 404, such as, from one or more target surrogates. The motion data includes a motion profile or distribution of at least the target in three dimensions.

A motion-compensated dose distribution for the target is calculated 406 using the motion data and the planned dose distribution. In certain embodiments, the calculating 406 includes estimating 408 motion of the target surrogates relative to a planning image used to generate a treatment fraction of the sample. Thereafter, for each of the at least one of the treatment fractions, using the motion estimates of the treatment fraction to generate 410 probability density functions (PDFs) for the target. Each of the PDFs represents a cumulative motion pattern of the target during the corresponding treatment fraction. Finally, motion compensated dose distributions are generated 412 from the PDFs. Suitably, this includes, for each of the PDFs, convolving the planned dose distribution corresponding to a stationary target irradiated with a radiation therapy beam with a margin as set forth in the RTP with the PDF to determine a motion-compensated dose for the treatment fraction, i.e., the dose which due to the motion was actually delivered. For example, the components of motion in a plane orthogonal to each therapy beam trajectory can be used to generate a 2D PDF which is used to determine how motion affected the delivered dose along that beam trajectory. Recognizing that the motion does not affect all beam trajectories the same enables the cumulative dose over all the trajectories or linear positions of the fraction to be calculated more accurately.

Once the motion-compensated dose distribution is calculated, it is compared 414 to the planned dose distribution. In certain embodiments, the comparison is qualitative and done via a side by side display of the motion-compensated dose distribution with the planned dose distribution. In such embodiments, comparison data from the user input devices 108 is suitably received indicating dosimetric differences between the dose distributions. In other embodiments, the comparison is quantitative. In such embodiments, it is contemplated that a difference between the motion-compensated dose distribution and the planned dose distribution is calculated. Additionally or alternatively, it is contemplated that at least one of dose volume histograms (DVH), maximum dose, mean dose, and minimum dose for each of the motion-compensated dose distribution and the planned dose distribution is calculated. Additionally or alternatively, it is contemplated that a dosimetric impact of motion on the RTP is calculated through a weighted combination of at least one of maximum dose, mean dose, and minimum dose for the motion-compensated dose distribution and/or the planned dose distribution. Given the cumulative dose actually delivered to this point in the RTP, the RTP is recalculated for the remaining fractions in order to deliver the total planned dose by the end of the treatment.

For recalculating the RTPs, the treatment margins are adjusted 416 based on dosimetric differences between the motion-compensated dose distribution and the planned dose distribution. Suitably, this includes identifying 418 cold spots and/or hot spots between the motion-compensated dose distribution and the planned dose distribution. Thereafter, at least one of the treatment margins nearest the cold spots are increased 420, and at least one of the treatment margins nearest the hot spots are decreased 422, e.g., by adjusting the collimator settings along one or more of the therapy beam trajectories. Further, if the difference between the dose distributions is negligible, at least one of the treatment margins is decreased 424.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor-based controller includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; and a display includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A treatment planning system for generating patient-specific treatment margins, said system comprising:
    a radiation therapy device;
    one or more processors programmed to:
        receive a radiation treatment plan (RTP) for irradiating a target over a course of one or more treatment fractions, said RTP including one or more treatment margins around the target and a planned dose distribution to be delivered to the target;
        receive motion data for at least one of the treatment fractions of the RTP;
        calculate a motion-compensated dose distribution for the target using the motion data to adjust the planned dose distribution based on the received motion data;
        compare the motion-compensated dose distribution to the planned dose distribution;
        adjust the one or more treatment margins based on dosimetric differences between the motion-compensated dose distribution and the planned dose distribution to generate the patient-specific treatment margins, the adjusting including:
            identifying cold spots and/or hot spots between the motion-compensated dose distribution and the planned dose distribution;
            in response to identifying a cold spot, increasing at least one of the treatment margins nearest the cold spot;
            in response to identifying a hot spot, decreasing at least one of the treatment margins nearest the hot spot;
            in response to negligible dose differences between the motion-compensated dose distribution and the planned dose distribution, decreasing at least one of the treatment margins; and
        control the radiation therapy device to deliver the patient-specific radiation treatment plan.

2. The system according to claim 1, wherein the one or more processors are further programmed to adjust the one or more treatment margins after or during one or more of the treatment fractions.

3. The system according to claim 1, wherein the calculating includes:
    creating one or more probability density functions (PDFs) from the motion data, each of said PDFs representing a cumulative motion pattern of the target during a treatment fraction.

4. The system according to claim 3, wherein the calculating further includes:
    convolving planned dose distributions with the PDFs to determine one or more motion-compensated doses indicative of an actually delivered dose actually delivered to the target.

5. The system according to claim 1, further including:
    a display;
    wherein the comparing includes at least one of:
        controlling the display to display the motion-compensated dose distribution adjacent to the planned dose distribution on the display; and,
        controlling the display to display the motion-compensated dose distribution overlaid on the planned dose distribution.

6. The system according to claim 1, wherein the comparing includes:
    calculating a difference between the motion-compensated dose distribution and the planned dose distribution; and/or
    calculating at least one of dose volume histograms (DVH), maximum dose, mean dose, and minimum dose for each of the motion-compensated dose distribution and the planned dose distribution.

7. The system according to claim 1, wherein the RTP is optimized for one of external beam radiation therapy, proton therapy, ablation therapy and high-intensity focused ultrasound therapy.

8. A radiation therapy system, said system comprising:
one or more imaging modalities that obtain one or more planning images;
a planning system according to claim 1, configured to generate the radiation treatment plan (RTP) for irradiating the target over the course of the treatment fractions from the planning images, said RTP including the one or more treatment margins around the target and the planned dose distribution for the target, and configured to generate patient-specific treatment margins from the RTP.

9. A method for generating patient-specific treatment margins, said method comprising:
receiving a radiation treatment plan (RTP) for irradiating a target over a course of one or more treatment fractions, said RTP including one or more planned treatment margins around the target and a planned dose distribution for the target;
receiving motion data for at least one of the treatment fractions of the RTP wherein the motion data is received during one of or between two of the one or more treatment fractions;
calculating a motion-compensated dose distribution for the target using the motion data to adjust the planned dose distribution based on the received motion data;
comparing the motion-compensated dose distribution to the planned dose distribution;
adjusting the treatment margins based on dosimetric differences between the motion-compensated dose distribution and the planned dose distribution to generate the patient-specific treatment margins,
wherein the adjusting includes:
identifying cold spots and/or hot spots between the motion-compensated dose distribution and the planned dose distribution;
in response to identifying a cold spot, increasing at least one of the treatment margins nearest the cold spot;
in response to identifying a hot spot, decreasing at least one of the treatment margins nearest the hot spot;
in response to negligible dose differences between the motion-compensated dose distribution and the planned dose distribution, decreasing at least one of the treatment margins; and controlling a radiation therapy device to deliver the motion-compensated dose distribution.

10. The method according to claim 9, wherein the calculating includes:
creating one or more probability density functions (PDFs) from the motion data, each of said PDFs representing a cumulative motion pattern of the target during a corresponding treatment fraction of the one or more treatment fractions; and,
convolving planned dose distributions with the PDFs to determine one or more motion-compensated doses indicative of a dose actually delivered to the target during the corresponding treatment fraction.

11. The method according to claim 10, wherein the calculating further includes:
accumulating the motion-compensated doses of the at least one of the treatment fractions.

12. The method according to claim 9, wherein the comparing includes at least one of:
displaying the motion-compensated dose distribution adjacent to the planned dose distribution;
displaying the motion-compensated dose distribution overlaid on the planned dose distribution; and,
calculating a difference between the motion-compensated dose distribution and the planned dose distribution.

13. The method according to claim 9, wherein the comparing includes at least one of:
calculating at least one of dose volume histograms (DVH), maximum dose, mean dose, and minimum dose for each of the motion-compensated dose distribution and the planned dose distribution; and,
calculating a dosimetric impact of motion on the RTP through a weighted combination of at least one of maximum dose, mean dose, and minimum dose for the motion-compensated dose distribution and/or the planned dose distribution.

14. A radiation therapy system comprising:
a radiation therapy apparatus configured to deliver radiation therapy in accordance with an RTP;
a motion monitor configured to generate motion data from target surrogates of a target; and,
one or more processors programmed to perform the method according to claim 9.

15. A non-transitory computer-readable medium carrying software which controls one or more processors to perform the method according to claim 9.

* * * * *